US009259214B2

(12) United States Patent
Galvani

(10) Patent No.: US 9,259,214 B2
(45) Date of Patent: Feb. 16, 2016

(54) SURGICAL RETRACTOR APPARATUS AND METHOD

(75) Inventor: Carlos A. Galvani, Tucson, AZ (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 128 days.

(21) Appl. No.: 13/107,506

(22) Filed: May 13, 2011

(65) Prior Publication Data
US 2011/0282159 A1    Nov. 17, 2011

Related U.S. Application Data

(60) Provisional application No. 61/334,275, filed on May 13, 2010.

(51) Int. Cl.
*A61B 17/02*    (2006.01)
*A61B 17/122*   (2006.01)
*A61B 17/00*    (2006.01)

(52) U.S. Cl.
CPC ......... *A61B 17/0218* (2013.01); *A61B 17/1227* (2013.01); *A61B 2017/00283* (2013.01); *A61B 2017/0287* (2013.01)

(58) Field of Classification Search
USPC ............................ 600/215–219; 606/157, 158
See application file for complete search history.

(56) References Cited

U.S. PATENT DOCUMENTS

| 5,785,649 | A | * | 7/1998 | Fowler, Jr. | 600/233 |
| 5,807,378 | A | * | 9/1998 | Jensen et al. | 606/1 |
| 5,964,698 | A | * | 10/1999 | Fowler | 600/217 |
| 6,631,538 | B1 | * | 10/2003 | Carr | 24/299 |
| 2004/0254427 | A1 | * | 12/2004 | Fowler, Jr. | 600/210 |
| 2006/0260105 | A1 | * | 11/2006 | Votel | 24/545 |
| 2009/0198107 | A1 | * | 8/2009 | Park et al. | 600/215 |

OTHER PUBLICATIONS

The NPL "Single-Incision Sleeve Gastrectomy Using a Novel Technique for Liver Retraction") publish Apr. 2010 on http://www.ncbi.nlm.nih.gov/pmc/articles/PMC3043573/.*
Galvani, et al., JSLS (2010) 14:228-233, Single-Incision Sleeve Gastrectomy Using a Novel Technique for Liver Retraction.

* cited by examiner

Primary Examiner — Samuel Hanna
(74) Attorney, Agent, or Firm — Husch Blackwell LLP

(57) ABSTRACT

An internal retractor has a clamp, a retractor hook and a universal joint therebetween. The internal retractor has a transverse dimension insertable through a cannula, and a longitudinal dimension deployable to retract user selectable organs. The internal retractor may be elongable. The internal retractor clamp may be closed in its rest position. The internal retractor clamp may be atraumatic. The internal retractor hook may be traumatic.

1 Claim, 3 Drawing Sheets

SURGICAL RETRACTOR APPARATUS AND METHOD

CROSS REFERENCE TO RELATED APPLICATIONS

This application claims priority to U.S. Provisional Patent Application 61/334,275 filed May 13, 2010.

BACKGROUND OF THE INVENTION

1. Field of the Invention

The field of the present invention is in medical surgeries, laparoscopic and minimally invasive endoscopic surgeries in particular.

2. Related Art

Most surgeries require retraction of various tissues and organs during the course of the surgery in order to properly expose the organ needing treatment and surgical repair. Traditional surgery with a large working space provided by a large entry incision allowed physicians or their assistants to reach into the surgical field with large retractor instruments and secure the subject organ or tissue and hold it securely out of the surgeon's way as he or she proceeds to the organ requiring surgical treatment.

In recent years, the advantages of laparoscopic surgery have made such minimally invasive procedures more and more common. In particular, single incision laparoscopic surgeries ("SILS") have been increasing due to both the cosmetic and therapeutic advantages of creating only one incision. The corresponding disadvantage of single incision laparoscopic surgeries in particular and laparoscopic surgeries in general is the reduced access of the surgeon and medical personnel to the surgical field and the consequent difficulty in executing otherwise routine surgical steps such as retraction. An example of a surgery highlighting these issues is single incision laparoscopic sleeve gastrectomy.

One of the operative requirements for all instruments being used in laparoscopic surgery in general and single incision laparoscopic surgery in particular is that the instruments and tools fit through a cannula which is in lay terms the long tube through which the surgeon enters the surgical space, frequently the abdomen, and through which tools are inserted and work is done. This operative requirement means that prior art normal retraction tools such as clamps or hooks cannot be used because they would occupy the space in the cannula that is needed for surgical tools such as pinchers, graspers, forceps, scalpels and energy devices. The prior art solution has been to make a second incision through which required instruments like retractors may be inserted in place. Therefore, in order to avoid a second incision, a retractor is needed that may be inserted through a cannula placed to achieve its useful purpose, and then maintain retraction entirely independently and entirely within the patient's body.

Prior art attempts to meet these needs have resulted in instruments that are cumbersome, complex and have a limited range of useful applications. For some procedures, such as single incision laparoscopic sleeve gastrectomies, previously developed instrumentation tools and retractors are not effective for the particular needs of that surgery, for example, retracting the left lobe of the liver in order to properly expose the stomach for the procedure at hand. Finally, time is always at a premium during surgery. Promoting speed without sacrificing accuracy or proper tissue handling is always advantageous. Hence, a device requiring fewer steps for execution of its use is advantageous.

SUMMARY OF THE INVENTION

The present invention is an internal retractor comprising a clamp, a retractor hook and a universal joint between them.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

Figure 1:
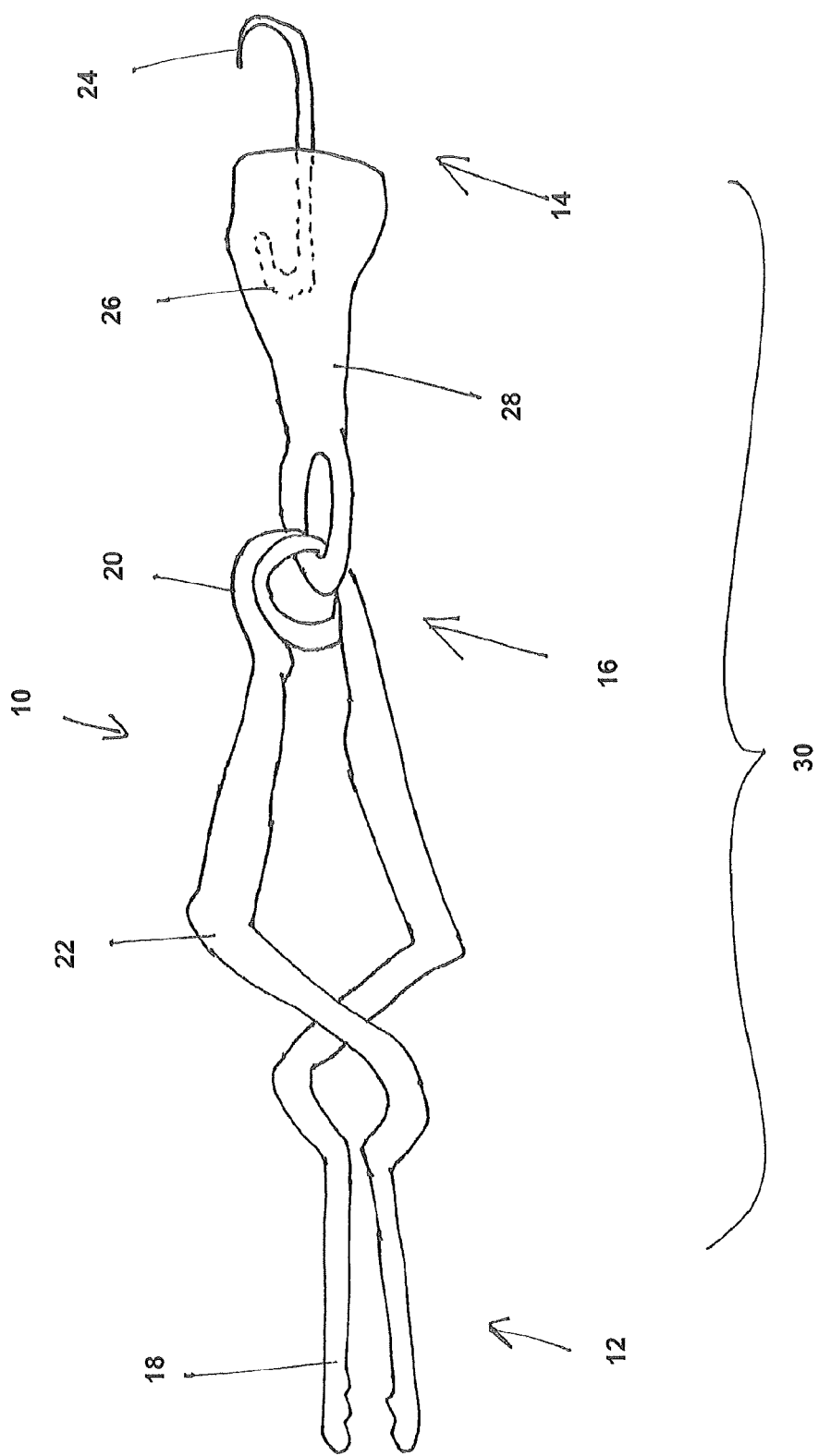
FIG. 1 is a side view of the internal retractor of the present invention.
Figure 2:
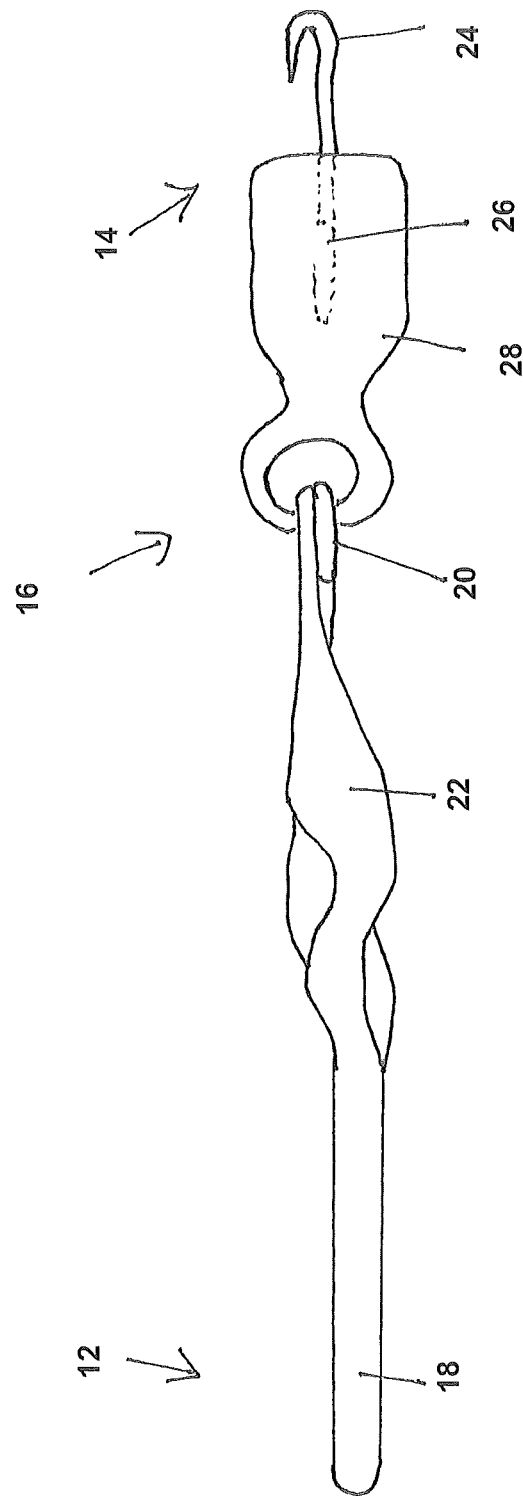
FIG. 2 is a top view of the internal retractor of the present invention.

Referring now to the drawings wherein like numbers refer to like elements, the internal retractor 10 of the present invention is comprised generally of a clamp 12, a hook 14, and a universal joint 16 between them. In the depicted embodiment, the clamp 12 has an engaged, closed position and a disengaged, open position depicted in FIG. 1. The clamp 12 includes pinchers 18, and a spring 20 which biases the clamp 12 into its engaged or closed position. The clamp 12 also includes engagement surfaces 22 by which a surgeon may clasp the engagement surfaces 22 for opening the clamp to its disengaged, open position. In the depicted embodiment, a bull dog clamp is used, such as a variety of clamps available from Aesculap Clamp™ in Tuttlingen, Germany.

The hook 14 of the present invention is comprised of a hook section 24 in embedded section 26 in an embedding material 28. In the depicted embodiment, the hook may be a Lone Star™ retractor hook from Lone Star Medical Products in Stafford, Tex. The embedding material 28 may be silicone. A medical grade latex-free silicone band offers a range of retractor placement options. The hook may be fixed to the end of the universal joint and may not slide in any direction to prevent unwanted piercing of the hook in tissues and facilitate surgeons' handling of the hook into the abdominal cavity.

Universal joint 16 between the clamp 12 and the hook 14 is affected by a loop of the embedding material 28 through the loop of the spring 20 in the clamp section, which is metal, in the depicted embodiment. The intra-engaged loops provide for a universal joint that may pivot or rotate in any direction, imparting an advantageous flexibility to the retractor. In the depicted embodiment, the silicone embedding material 28 provides for some degree of elongation of the overall instrument, together with some tensile force biasing the hook and clamp closer together, and accordingly, providing the advantageous, harmless retracting tension on the organs to which it is attached or against which it is deployed.

In the depicted embodiment, the sharp hook 24 is traumatic, that is, pointed so that it may be used by piercing of tissue in order to place the hook in that tissue. The clamp of course is atraumatic. The depicted embodiment has atraumatic DeBakey serrations for secure tissue clamping without trauma. Clamps of the depicted variety advantageously exert the same defined pressure.

Figure 3:
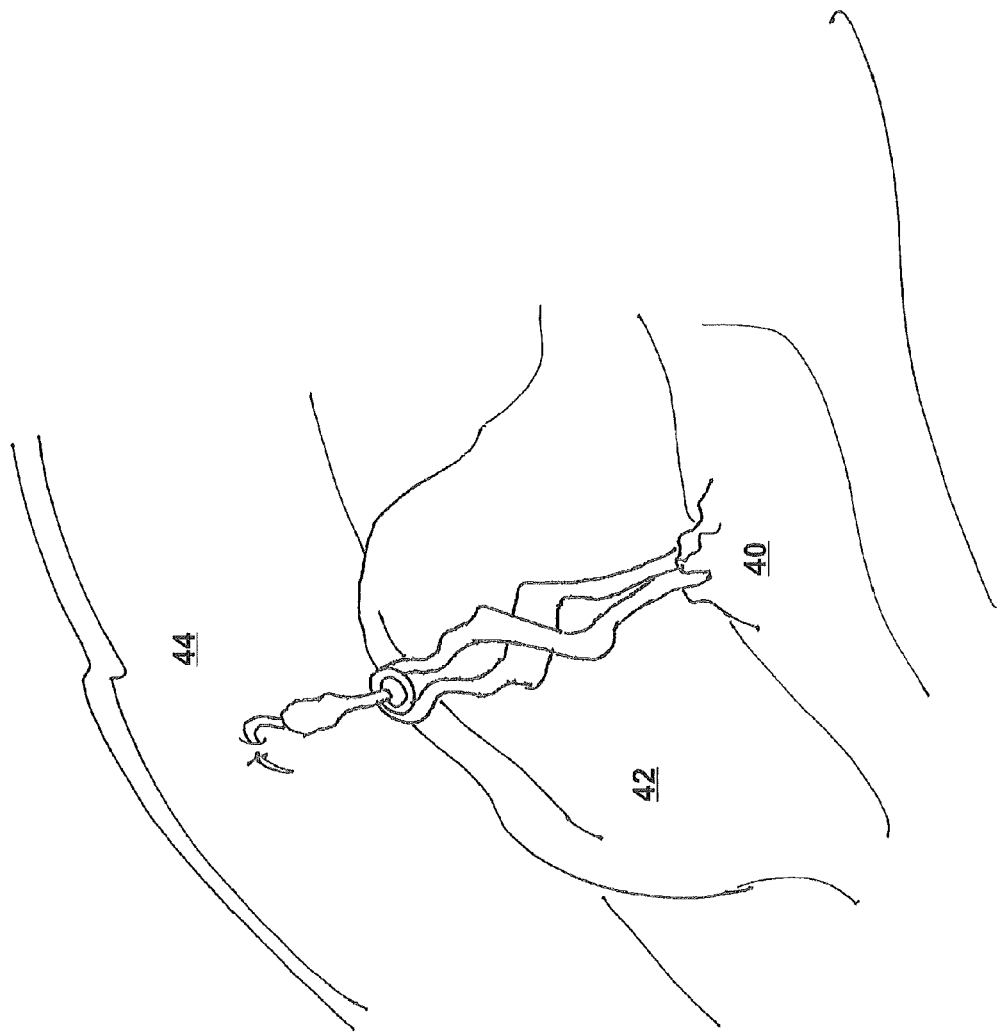
FIG. 3 is a first view of an internal retractor of the present invention clamped below the left lobe of the liver during a single incision laparoscopic sleeve gastrectomy and traumatically (sharply) hooked to the inner surface of the abdominal wall.

In use, the internal retractor hook is placed in the cannula's external end and inserted into the body cavity, which is pneumatically inflated to provide working space as is known in the art. The instrument may be advantageously inserted with the hook being placed between the jaws of the clamp, to prevent the hook getting caught in the internal side of the cannula or in unwanted tissues of the body. To place the retractor in the body, the surgeon inserts into the work space a surgical pincer or forceps which may be used to grasp the engaging surfaces 22 in the clamp. The clamp is then placed on or near the organ to be retracted in an exact location at the surgeon's discretion. For example, in FIG. 3, the clamp is used to clamp the pars flaccida 40 underneath the left lobe of the liver 42. Clamping is achieved of course by applying pressure to the engaging surfaces 22 in order to open the clamp tongs 18, which are placed around the tissue to be clamped. Then engaging pressure on the engaging surfaces 22 is released whereupon the closing bias of the spring 20 engages the tongs 18 to the tissue. The surgeon has a choice of application forceps for straight or angled clamp application; this facilitates clamping of the desired organ.

Thereafter the surgeon clasps the other end of the tool, the hook 24, and uses the middle portion along the side of the tool 30, to retract the intended tissue, which in the depicted embodiment is the left lobe of the liver 42. Having achieved the advantageous exposure in the operative field, the hook is placed in order to retain the left lobe of the liver 42 in the retracted position. The placement of the traumatic hook 24 is by piercing the inner surface of the abdominal wall 44 at the proper position. The hook needle reliably secures attachment to the parietal peritoneum. Thereafter, the instrument may be completely released. The middle portion 30 of the tool rests against the left lobe of the liver 42 holding it out of place and the tension between the pars flaccida 40 at the clamp end and the abdominal wall 44 at the hook end maintain the left lobe of the liver in the retracted position. The organ to be retracted can be manipulated as required and brought into a favorable position for the relevant stage of the operation. Two clips can be applied if necessary. Thereafter the surgeon may perform the surgery. Those of skill in the art will appreciate the reduced number of steps for application of the apparatus of the present invention relative to more complex prior art devices, and the broader range of situations in which it may be used relative to other prior art devices. The retraction clip does not block any trocar access during application, since the application forceps can be withdrawn after the clip has been applied facilitating single incision surgery.

After the surgery, the process is simply reversed with the hook 24 being removed from the abdominal wall, the surgical grasping instrument reengaged with the engaging surfaces 22 of the clamp 12 in order to open the tongs 18 and release the clasped clamped tissue. Thereafter the tool may be grasped at another position, for example at hook 24, for extraction through the cannula.

The internal retractor is advantageously adaptable, reliable, safe and easy to use. Its use lessens some of the natural challenges of SILS. The apparatus of the invention is versatile, reusable, reduces the numbers of incisions, and is readjustable. In addition, several retractors can be added if necessary.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

I claim:

1. A surgical retractor for retracting internal organs comprising:
    a single-piece, atraumatic clamp positioned at a first end of the surgical retractor, said single-piece clamp being operable with surgical forceps, said single-piece clamp consisting of two opposing pinchers at a proximal portion of said single-piece clamp, and a spring portion at a distal portion of said single-piece clamp opposite said two pinchers configured to allow the two pinchers to pivot relative to one another about said spring portion, said two pinchers including rounded smooth ridges on internal surfaces so as to remain atraumatic when clamped onto tissue and said spring portion defining a ring which biases the two pinchers of said single-piece clamp towards each other in a closed position;
    a traumatic hook retractor consisting of a hook having a sharp pointed tip at a distal portion of said hook retractor and a silicone body portion at a proximal portion of said hook retractor, said hook including an embedded section embedded in said silicone body portion, said silicone body portion including an eyelet defined through said silicone body portion of said hook retractor;
    a universal joint positioned between and coupling the two pinchers of the single-piece clamp and the hook of the hook retractor to one another, said universal joint allowing pivotal or rotational motion between said single-piece clamp and said hook retractor in any direction, said universal joint formed by securely coupling said eyelet of said silicone body portion of said hook retractor to said ring defining the spring portion of said single-piece clamp such that said eyelet and said ring are intra-engaged with one another;
    wherein said silicone body portion is stretchable to provide some degree of elongation of the surgical retractor with some tensile force biasing the single-piece clamp and the hook retractor closer together, such that an axial distance between the single-piece clamp and the hook of the hook retractor changes due to the elasticity of the silicone body portion;
    said surgical retractor having a maximum width in a transverse dimension insertable through a cannula having a diameter appropriate for minimally invasive surgery, and a longitudinal dimension deployable to retract user selectable organs, wherein said transverse direction is transverse to a longitudinal axis of the surgical retractor, and said longitudinal dimension is along the longitudinal axis of the surgical retractor; and
    wherein said surgical retractor is configured for use in minimally invasive surgery.

* * * * *